United States Patent [19]

Schurter et al.

[11] Patent Number: 4,875,926
[45] Date of Patent: Oct. 24, 1989

[54] 3-FLUOROPYRIDYL-2-OXY-PHENOXY DERIVATIVES HAVING HERBICIDAL ACTIVITY

[75] Inventors: Rolf Schurter, Binningen; Peter J. Diel, Riehen, both of Switzerland

[73] Assignee: Ciba-Geigy Corporation, Ardsley, N.Y.

[21] Appl. No.: 150,680

[22] Filed: Feb. 1, 1988

Related U.S. Application Data

[62] Division of Ser. No. 844,407, Mar. 26, 1986, Pat. No. 4,740,235.

[30] Foreign Application Priority Data

Apr. 1, 1985 [CH] Switzerland ............... 1401/85

[51] Int. Cl.$^4$ ............... C07D 213/56; A01N 43/40
[52] U.S. Cl. ............... 71/94; 546/291; 546/302
[58] Field of Search ............... 546/291, 302; 71/94

[56] References Cited

U.S. PATENT DOCUMENTS 4,325,729  4/1982  Rempfler et al. ............... 71/94
4,491,468  1/1985  Johnston et al. ............... 71/94
4,565,568  1/1986  Johnston et al. ............... 71/94

Primary Examiner—Alan L. Rotman
Attorney, Agent, or Firm—Kevin T. Mansfield; Edward McC. Roberts

[57] ABSTRACT

There are described novel 3-fluoropyridyl-2-oxy derivatives having a herbicidal action and an action reducing the growth of grasses, which compounds correspond to the formula I

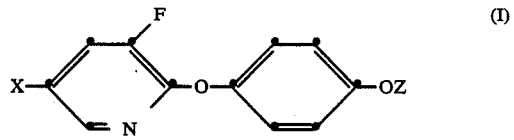

wherein
X is halogen or the trifluoromethyl group, and
Z is an alkanoic acid derivative which is more precisely described in the specification.

These compounds are suitable for the selective control of weeds in crops of cultivated plants, or for the reduction of the growth of grasses.

7 Claims, No Drawings

3-FLUOROPYRIDYL-2-OXY-PHENOXY DERIVATIVES HAVING HERBICIDAL ACTIVITY

This is a divisional of application Ser. No. 844,407 filed on Mar. 26, 1986, now U.S. Pat. No. 4,740,235.

In the published European patent application No. EP-A-83 556, there have already been described 3-fluoropyridyl-2-oxy-phenoxy derivatives having herbicidal activity, which correspond to the formula

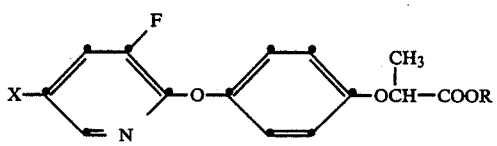

wherein Q is oxygen or sulfur, R is, inter alia, hydrogen, a metal or ammonium ion, or an unsubstituted or substituted $C_1-C_9$-alkyl, $C_3-C_9$-cycloalkyl, $C_3-C_9$-alkenyl or $C_3-C_9$-alkynyl group, or a $C_3-C_9$-cycloalkenyl group or an imino group, and X is chlorine, bromine or iodine.

These compounds exhibited a good selective-herbicidal action in particular against gramineous weeds in crops of cultivated plants, such as cereals, maize, rice, cotton, soya bean and sugar beet.

It has been shown that a further group of novel 3-fluoropyridyl-2-oxy-phenoxy derivatives have an excellent selective-herbicidal action, both in the pre-emergence and post-emergence process, against in particular gramineous weeds in crops of cultivated plants.

The novel 3-fluoropyridyl-2-oxy-phenoxy derivatives correspond to the formula I

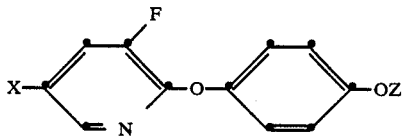

wherein

X is a halogen atom or the trifluoromethyl group, and

Z is an alkanecarboxylic acid radical $-CH(CH_3)Z^1$, $CH_2Z^2$, $-CH(C_2H_5)Z^2$, $-CH(CH_2OCH_3)Z^2$ or $-CH_2-CZ^3=CH_2$, in which $Z^1$ is a radical
—COQ—$(CR^1R^2)_n$—$(CR^3R^4)_m$—$Y^1$,
—$CONA^1A^2$,
—$CONA^1(OA^2)$,
—$COQCHA^3$—$COOA^4$,
—$C(OA^5)=NA^6$,
—$COC(COA^7)=CA^8(OA^9)$,
—$COOCA^8=CA^9$—$COA^7$,
—$CSQR$,
—$COQ$—$G$—$Y^2$,
$CO$—$PO(OR^{14})O_pR^{15}$,
—$COQ$—$G$—$A^{10}$,
—$COQ$—$G$—$A^{11}$, and
—$COQ$—$G$—$A^{12}$, $Z^2$ is a radical —COQR or is the same as $Z^1$, m is zero, 1 or 2, n is 1 or 2, $Z^3$ is a radical —$COOA^9$ or —CN, $Y^1$ is a radical —$CH(OR^{16})_2$, a benzoyl, benzylsulfonyl, benzylsulfinyl, naphthoyl or phenyl-$C_1-C_4$-alkyl-carbonyl radical, which is substituted in the phenyl ring by $R^7$ and $R^8$, or is a radical —$NR^{10}R^{11}$ or —$NR^{12}COQ^1R^{13}$, $Y^2$ is a radical —$OPQ^2(OR^{14})_2$, —$PO(OR^{14})(O)_pR^{15}$ or —$SiA^7(O_pR^{12})R^{13}$, Q, $Q^1$, $Q^2$ independently of one another are each oxygen or sulfur, is hydrogen or the equivalent of an alkali metal, alkaline-earth metal, copper or iron ion, or is a quaternary $C_1-C_4$-alkylammonium or $C_1-C_4$-hydroxyalkylammonium radical, $C_1-C_9$-alkyl, straight-chain or branched-chain, unsubstituted or substituted by halogen, hydroxyl, cyano, nitro, phenyl, $C_1-C_4$-alkoxy-$(C_1-C_4$-alkoxy$)_q$ or a radical —$COOR^5$, —$COSR^5$, —$CON(R^5)_2$, —$NR^5R^6$ or —$NR^5R^9R^6 \oplus M\ominus$, or is $C_3-C_9$-cycloalkyl, an unsaturated aliphatic or alicyclic radical which can contain N and which contains 2-9 C atoms and at least one double or triple bond, or is phenyl, unsubstituted or substituted by halogen, $C_1-C_4$-alkyl, $C_1-C_4$-alkoxy, CN, $COCH_3$ or a radical —$COOR^5$, —$COSR^5$ or —$CONR^5R^6$, $R^1$, $R^2$, $R^3$, $R^4$ independently of one another are each hydrogen, $C_1-C_6$-alkyl or phenyl, $R^5$ is hydrogen, $C_1-C_6$-alkyl, $C_1-C_6$-haloalkyl, $C_2-C_8$-alkoxyalkyl, $C_3-C_6$-alkenyl, $C_3-C_6$-haloalkenyl or $C_3-C_6$-alkynyl, $R^6$ is the same as $R^5$, or is a phenyl or benzyl radical which is unsubstituted or substituted by halogen, $C_1-C_4$-alkyl, $C_1-C_4$-alkoxy, CN, $NO_2$, $COCH_3$, —$COOR^5$, —$COSR^5$ or —$CON(R^5)_2$, $R^7$, $R^8$ independently of one another are each hydrogen, $C_1-C_4$-alkyl, $C_1-C_4$-alkoxy, halogen, $CF_3$, $NO_2$, CN, —CO—$(C_1-C_4$-alkyl) or —$COO(C_1-C_4$-alkyl), $R^9$ is the same as $R^5$ but is independent thereof, $R^{10}$, $R^{11}$ together are $C_2-C_5$-alkylene radicals, which form together with the nitrogen atom to which they are linked a saturated 5- or 6-membered heterocycle, which can additionally contain an oxygen or sulfur atom or a group —$NR^{12}$, $R^{12}$, $R^{13}$ are each $C_1-C_6$-alkyl, $R^{14}$, $R^{15}$ independently of one another are each hydrogen, $C_1-C_4$-alkyl, $C_3-C_4$-alkenyl, $C_3-C_4$-alkynyl, $C_2-C_4$-haloalkyl, $C_1-C_4$-alkoxy-$(C_2-C_4)$-alkyl, $C_1-C_4$-cyanoalkyl, or a phenyl, phenyl-$(C_1-C_4)$-alkyl or naphthyl radical, which is unsubstituted or mono- or disubstituted by halogen, $C_1-C_4$-alkyl, $C_1-C_4$-alkoxy, $C_1-C_4$-haloalkyl, $C_1-C_4$-haloalkoxy, nitro or cyano, where p is 0 or 1, and q is 0 or a number from 1-4, and $R^{15}$ is not H when p is 0, $R^{16}$ is $C_1-C_4$-alkyl, or the two radicals $R^{16}$ together form a branched-chain or straight-chain $C_2-C_8$-alkylene chain, M is the anion of an organic or inorganic acid, $A^1$, $A^2$ are the same as $R^5$ or $R^6$ but are independent thereof, or $C_2-C_6$-alkenyl groups which together with the nitrogen atom form a saturated 5- or 6-membered heterocyclic ring, $A^3$, $A^4$ are $C_1-C_4$-alkylene groups, which together with the CHCOO group form a 5- or 6-membered lactone, $A^5$, $A^6$ are $C_1-C_4$-alkylene groups, which together with the grouping to which they are linked form an unsaturated heterocyclic ring, $A^7$ is $C_1-C_6$-alkyl or $C_1-C_6$-alkoxy, $A^8$ is hydrogen or $C_1-C_6$-alkyl, $A^7$ and $A^8$ are a $C_1-C_6$-alkylene or -alkenylene bridge, $A^9$ is hydrogen or $C_1-C_4$-alkyl, $A^{10}$ is the radical

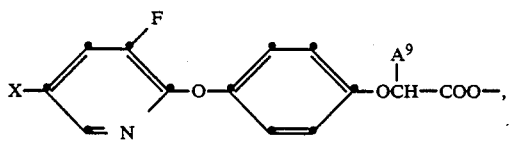

$A^{11}$ is the radical

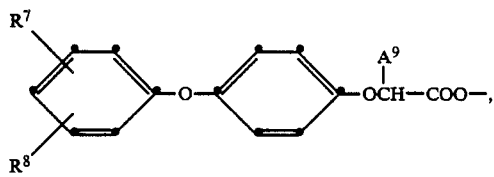

$A^{12}$ is the radical

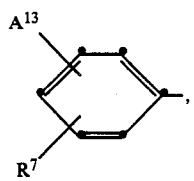

$A^{13}$ is $C_1$-$C_4$-alkyl, $C_1$-$C_4$-alkoxy, halogen, $CF_3$, —CO($C_1$-$C_4$-alkyl) or —COO($C_1$-$C_4$-alkyl), and G is a $C_1$-$C_3$-alkylene chain which can be mono- or disubstituted by a substituent from the group methyl and phenyl.

The above definition of G embraces methylene, 1,2-ethylene and 1,3-propylene, and the groups derived therefrom by substitution of 1 or 2 hydrogen atoms by methyl or phenyl, for example: ethylidene, isopropylidene (2,2-propylidene), benzylidene, 1-phenylethylidene, diphenylmethylene, 1,2-propylene, 2,3-butylene, 1,1-dimethyl-1,2-ethylene, 1,1-diphenyl-1,2-ethylene, 1,2-diphenyl-1,2-ethylene, 1-methyl-1-phenyl-1,2-ethylene, 1,2-butylene, 1,3-butylene, 2,2-dimethyl-1,3-propylene, 1-methyl-1-phenyl-1,3-propylene, 1,2-diphenyl-1,3-propylene and 1,3-diphenyl-1,3-propylene.

When the alkanecarboxylic acid radical Z contains an asymmetrically substituted carbon atom (for example —CH($CH_3$)$Z^1$), there can exist two enantiomeric forms. The invention relates to both the racemates and the R- and S-enantiomers.

The 3-fluoropyridyl-2-oxy-phenoxy derivatives according to the invention are characterised by a good action against mono- and some dicotyledonous weeds; they are above all effective in the post-emergence process against undesirable weeds and wild grasses occurring in cultivated crops, such as crops of cereals, maize, rice, soya bean and sugar beet. A particularly valuable aspect is that it is possible with the novel derivatives to combat wild grasses which are otherwise very difficult to control, for example Avena fatua, Avena sterilis, Alopecurus myosuroides, Lolium perenne, Phalaris sp., Bromus tectorum and various species of Setaria and Panicum. The action under field conditions is achieved even with small applied amounts of less than 1 kg per hectare, at which levels the cultivated crops are not harmed, or are harmed to only a negligible extent.

Halopyridyloxy-α-phenoxy-propionic acid derivatives have been described in numerous publications (cp. for example the German Offenlegungsschriften Nos. 2,546,251, 2,649,706, 2,714,622 and 2,715,284, and the European Publications Nos. 483 and 1473). In these publications, the 3-fluoropyridyl-2-oxy-phenoxy derivatives according to the present invention have in part been taken into account and concomitantly included in the scope. Compounds of this type have never however been produced or tested. They are distinguished from the known halopyridyloxy-60-phenoxy-propionic acids by a stronger action, and hence by the fact that it is possible to use them effectively in smaller amounts. Where the applied amount is sufficiently great however, there also occurs a total-herbicidal action. The novel compounds according to the invention can be applied both in the pre-emergence process and in the post-emergence process. The amounts applied can vary within wide limits, for example between 0.05 and 5 kg of active substance per hectare.

Furthermore, the compounds of the formula I have favourable growth-regulating effects (growth inhibition). They inhibit in particular the growth of grasses.

3-Fluoropyridyl-2-oxy-phenoxy derivatives of the formula I which have proved very active are those which correspond to the formula Ia

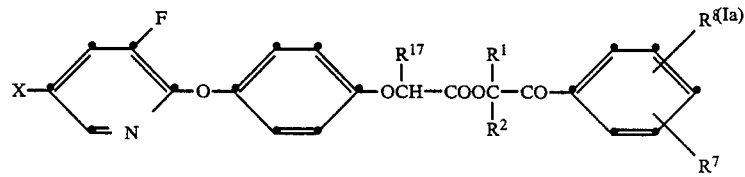

wherein $R^1$, $R^2$, $R^7$, $R^8$ and X have the meanings defined under the formula I, and $R^{17}$ is hydrogen, $C_1$-$C_2$-alkyl or methoxymethyl; and particularly those compounds in which $R^1$ and $R^2$ are hydrogen or methyl, $R^{17}$ is methyl and X is chlorine or trifluoromethyl: more especially the α-[4-(5-chloro-3-fluoropyridyl-2-oxy)-phenoxy]-propionic acid benzoylmethyl ester and the α-[4-(5-chloro-3-fluoropyridyl-2-oxy)-phenoxy]-propionic acid-1-benzoylethyl ester.

Also the 3-fluoropyridyl-2-oxy-phenoxy derivatives of the formula Ib

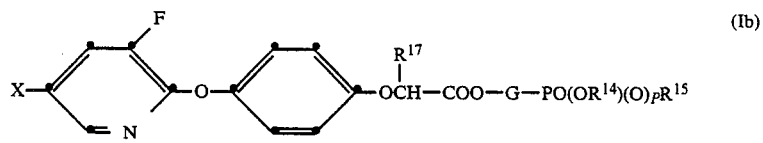

wherein X, G, $R^{14}$, $R^{15}$ and p have the meanings defined under the formula I, and $R^{17}$ is hydrogen, $C_1$–$C_2$-alkyl phenoxy]-propionic acid-(2-oxo-tetrahydrofurfuryl-3-yl) ester; and those compounds of the formula Ie

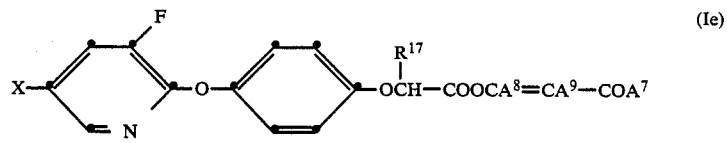

or methoxymethyl; and particularly those compounds in which X is chlorine or trifluoromethyl, G is $C_1$–$C_3$-alkylene, $R^{14}$ and $R^{15}$ are each methyl or ethyl, and $R^{17}$ is methyl.

Examples of these compounds are: (2-[4-(5-chloro-3-fluoropyridinyl-2-oxy)-phenoxy]-propionyl-oxy)-methylphosphonic acid diethyl ester, and (2-[4-(5-chloro-3-fluoropyridinyl-2-oxy)-phenoxy]-propionylwherein X, $A^7$, $A^8$, $A^9$ and $R^{17}$ have the meanings defined in the foregoing; especially those compounds in which X is chlorine or trifluoromethyl, $A^7$ and $A^8$ together form a $C_3$–$C_5$-alkylene bridge, $A^9$ is hydrogen and $R^{17}$ is methyl: in particular the α-[4-(3-fluoro-5-chloropyridyl-2-oxy)-phenoxy]-propionic acid-(5,5-dimethyl-3-oxo-cyclohex-1-en-1-yl) ester.

Of particular interest also are compounds of the formula If

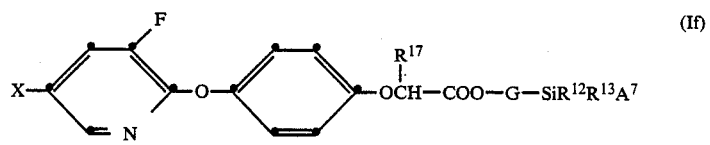

oxy)-methylphosphonic acid dimethyl ester.

In addition, compounds shown to be active are those of the formula Ic

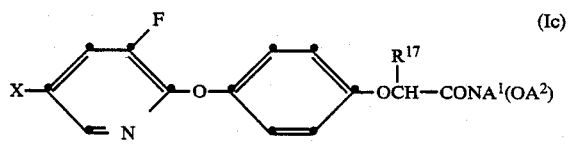

wherein X, $A^1$, $A^2$ and $R^{17}$ have the meanings defined in the foregoing; and especially those compounds in which X is chlorine or trifluoromethyl, $A^1$ is hydrogen, $C_1$–$C_3$-alkyl, $C_3$–$C_4$-alkylene or $C_3$–$C_4$-haloalkylene, $A^2$ is hydrogen or methyl, and $R^{17}$ is methyl: in particular 4-(5-chloro-3-fluoropyridyl-2-oxy)-phenoxyacetic acid methoxyamide and α-[4-(5-chloro-3-fluoropyridyl-2-oxy)-phenoxy]-propionic acid methoxyamide.

Further compounds which have proved interesting are those of the formula Id

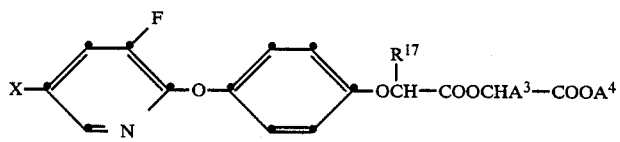

wherein X, $A^3$, $A^4$ and $R^{17}$ have the meanings defined in the foregoing; and especially those compounds in which X is chlorine or trifluoromethyl, $A^3$ and $A^4$ together form a $C_2$–$C_3$-alkylene bridge and $R^{17}$ is methyl: in particular α-[4-(3-fluoro-5-chloropyridyl-2-oxy)- wherein X, G, $R^{12}$, $R^{13}$ and $R^{17}$ have the meanings defined in the foregoing; more especially those compounds in which X is chlorine or trifluoromethyl, G is $C_1$–$C_3$-alkylene, and $R^{12}$, $R^{13}$ and $R^{17}$ are each methyl.

Examples of these compounds are:

α-[4-(5-chloro-3-fluoropyridyl-2-oxy)-phenoxy]-propionic acid-trimethylsilyl-methyl ester, α-[4-(5-chloro-3-fluoropyridyl-2-oxy)-phenoxy]-propionic acid-2'-trimethylsilyl-eth-1'-yl ester, α-[4-(3-fluoro-5-trifluoromethyl-pyridyl-2-oxy)-phenoxy]-propionic acid-2'-trimethylsilyl-eth-1'-yl ester, and α-[4-(3-fluoro-5-trifluoromethyl-pyridyl-2-oxy)-phenoxy]-propionic acid-trimethylsilyl-methyl ester.

Likewise shown to be active are the compounds of the formula Ig

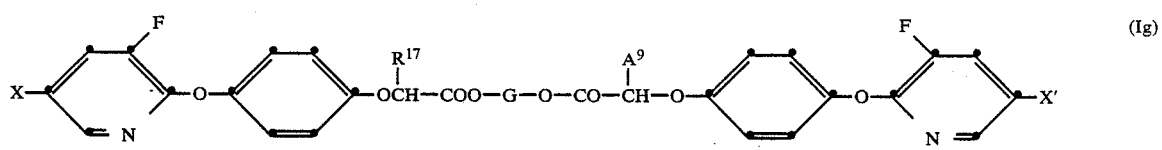

wherein X and X' are chlorine or trifluoromethyl, and $R^{17}$, $A^9$ and G have the meanings defined in the foregoing; more especially however those compounds in which G is $C_2$–$C_4$-alkylene, and $R^{17}$ and $A^9$ are methyl: in particular bis-α-[4-(5-chloro-3-fluoropyridyl-2-oxy)-phenoxy]-propionic acid glycol ester, and bis-α-[4-(3-fluoro-5-trifluoromethyl-pyridyl-2-oxy)-phenoxy]-propionic acid glycol ester.

Also the 3-fluoropyridyl-2-oxy-phenoxy derivatives of the formula Ih

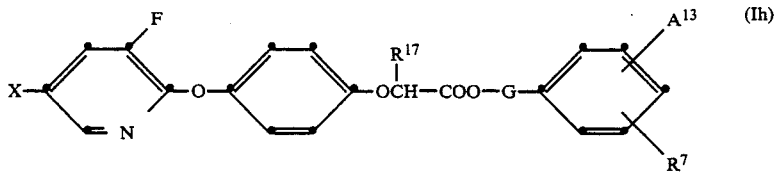

(Ih)

wherein X, G, $R^7$ and $A^{13}$ have the meanings defined under the formula I, and $R^{17}$ is hydrogen, $C_1$-$C_2$-alkyl or methoxymethyl; especially those compounds in which X is chlorine or trifluoromethyl, G is $C_1$-$C_3$-alkylene, $R^7$ is hydrogen, halogen or methyl, $A^{13}$ is halogen and $R^{17}$ is methyl: in particular the α-[4-(5-chloro-3-fluoropyridyl-2-oxy)-phenoxy]-propionic acid-4'-chlorobenzyl ester.

In addition, the 3-fluoropyridyl-2-oxy-phenoxy derivatives of the formula Ii

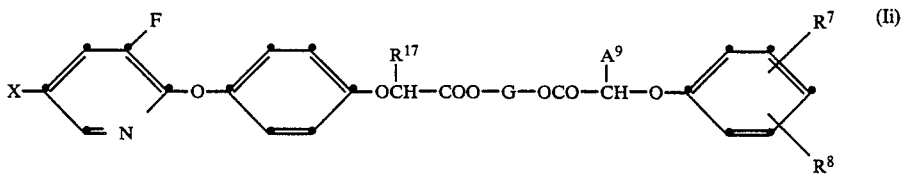

(Ii)

wherein X, G, $R^7$, $R^8$ and $R^9$ have the meanings defined under the formula I, and $R^{17}$ is hydrogen, $C_1$-$C_2$-alkyl or methoxymethyl; especially those compounds in which X is chlorine or trifluoromethyl, G is $C_1$-$C_4$-alkylene, $R^7$ and $R^8$ are hydrogen, halogen, methyl or $CF_3$, $A^9$ is hydrogen or methyl, and $R^{17}$ is methyl, in particular the 1-(2'-[4-(5-chloro-3-fluoropyridyl-2-oxy)-phenoxy]-propionic acid)-2-(4-chlorophenoxyacetic acid)-glycol ester.

The novel compounds of the formula I are produced by methods known per se.

The first of these processes comprises reacting a 2,3-difluoropyridine of the formula II

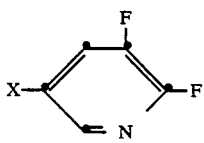

(II)

wherein X has the meaning defined under the formula I, in an inert solvent or diluent and in the presence of the equimolar amount of a base, with a 4-hydroxyphenoxy-α-alkanoic acid derivative of the formula III

(III)

wherein Z has the meaning defined under the formula I.

Another process comprises reacting a 4-(3-fluoropyridyl-2-oxy)-phenol of the formula IV

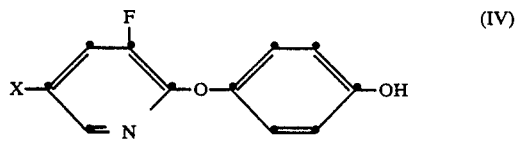

(IV)

wherein X has the meaning defined under the formula I, in an inert solvent or diluent and in the presence of the equimolar amount of a base, with a halide of the formula V Hal—Z (V)

wherein Hal is chlorine or bromine, and Z has the meaning defined under the formula I.

A further process comprises converting a 3-aminopyridyl-2-oxyphenoxy derivative of the formula VI

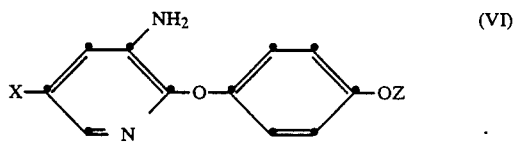

(VI)

wherein X and Z have the meanings defined under the formula I, using known methods, into a diazonium salt, and converting this further into the fluorine compound.

Finally, a process for producing the compounds of the formula I comprises reacting an acid halide of the formula VII

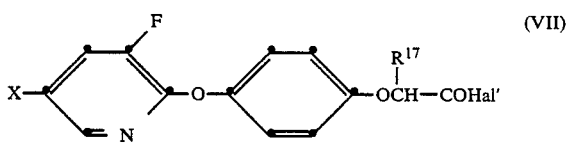

(VII)

wherein Hal' is fluorine, chlorine or bromine, and X and $R^{17}$ have the meanings defined in the foregoing, in an inert solvent or diluent and in the presence of an equimolar amount of a base, with an alcohol, thiol or amine.

By alcohol is meant, inter alia, the classes of compounds HQR and HQ—G—$PO(OR^{14})(O)_p(R^{15})$; and by amine is meant, inter alia, the classes of compounds such as $HNA^1A^2$ or $HNA^1(OA^2)$.

Some of these reactions are advantageously performed in an organic solvent or diluent inert to the reactants, for example in an alcohol, ester, ether or ketone, or in dimethylformamide, dimethyl sulfoxide or acetonitrile, or in an aromatic compound, such as benzyl, toluene, and so forth.

The reaction temperatures are between $-10°$ and $+150°$ C., in practice however between room temperature and the boiling point of the solvent. Depending on the chosen starting material, the solvent and the temperature, the reaction time is between one hour up to about one day.

Where a halogen atom is detached in the reaction, the equimolar amount of an acid-binding agent should be used. Suitable as such is essentially any inorganic or organic base, for example: NaOH, KOH, $NaHCO_3$, $K_2CO_3$ or K-tertbutylate, and amines, such as trimethylamine, triethylamine, pyridine, 4-dimethylaminopyridine, and so forth.

The novel active substances of the formula I are stable compounds which are soluble in customary organic solvents, such as alcohols, ethers ketones, dimethylformamide, dimethyl sulfoxide, and the like. They are not explosive or corrosive, and the handling of them requires no special precautionary measures.

The compounds of the formula I are used either in an unmodified form or preferably together with auxiliaries customarily employed in formulation practice, and are thus processed in a known manner for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting, scattering or pouring, and likewise the type of composition, are selected to suit the objectives to be achieved and the given conditions.

The formulations, that is to say, the compositions or preparations containing the active substance of the formula I and optionally a solid or liquid additive, are produced in a known manner, for example by the intimate mixing and/or grinding of the active substances with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones such as cyclohexanone, strongly polar solvents, such as N-methyl-2-pyrrolidone, dimethyl sulfoxide or dimethylformamide, as well as optionally epoxidised vegetable oils, such as epoxidised coconut oil or soybean oil; or water.

The solid carriers used, for example for dusts and dispersible powders, are as a rule natural mineral filers, such as calcite, talcum, kaolin, montmorillonite or attapulgite. In order to improve the physical properties, it is possible to add highly dispersed silicic acid or highly dispersed absorbent polymers. Suitable granulated adsorptive carriers are porous types, for example pumice, ground brick, sepiolite or bentonite; and suitable non-sorbent carriers are materials such as calcite or sand. There can also be used a great number of pre-granulated materials of inorganic or organic nature, such as in particular dolomite or ground plant residues.

Suitable surface-active compounds are, depending on the nature of the active substance of the formula I to be formulated, nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are for example the alkali metal, alkaline-earth metal or optionally substituted ammonium salts of higher fatty acids ($C_{10}$–$C_{20}$), for example the Na or K salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as rule in the form of alkali matal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included among these are also the salts of sulfuric acid esters and sulfonic acids of fatty alcohol ethylene oxide adducts. The sulfonated benzimidazole derivatives preferably contain 2 sulfonic acid groups and a fatty acid group having 8–22 C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4–14)-ethylene oxide adduct.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylene-diaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenol-polyethoxyethanols, castor oil polyglycol ethers, polypropylene/polyethyleneoxy adducts, tributylphenoxy-polyethoxyethanol, polyethylene glycol and octylphenoxy-polyethoxyethanol. Suitable also are fatty acid esters of polyoxyethylenesorbitan, such as polyoxyethylene-sorbitan-trioleate.

In the case of the cationic tensides, they are in particular quaternary ammonium salts which contain as N-substituents at least one alkyl group having 8 to 22 carbon atoms and, as further substituents, lower, optionally halogenated alkyl, benzyl or lower hydroxyalkyl groups. The salts are preferably in the form of halides, methyl sulfates or ethyl sulfates, for example stearyltrimethylammonium chloride or benzyldi(2-chloroethyl)ethylammonium bromide.

The tensides customarily used in formulation practice are described, inter alia, in the following publications:

"McCutcheon's Detergents and Emulsifiers Annual", MC Publishing Corp., Ridgewood, N.J., 1979;

H. Stache, "Tensid Taschenbuch", 2nd Edition, C. Hanser Verlag, Munich and Vienna, 1981; and M. and J. Ash, "Encyclopedia of Surfactants", Vol. I–III, Chemical Publishing Co., N.Y., 1980–81.

These preparations contain as a rule 0.1 to 99%, particularly 0.1 to 95%, of active substance of the formula I, 1 to 99% of a solid or liquid additive, and 0 to 25%, especially 0.1 to 25%, of a tenside.

Whereas commercial products are preferably in the form of concentrated compositions, the preparations employed by the end-user are as a rule diluted.

The compositions can also contain further additives, such as stabilisers, antifoaming agents, viscosity regulators, binders and adhesives, and also fertilisers or other active ingredients for obtaining special effects.

The following Examples describe in detail the production of the 3-fluoropyridyl-2-oxy-phenoxy derivatives of the formula I according to the invention, and of compositions containing such compounds as active ingredients. Further esters according to the invention which are obtained in an analogous manner are listed in the Tables following the Examples. Temperatures are given in degrees Centigrade and percentage values relate to weight.

EXAMPLE 1

Production of (±)-2-[4-(5-chloro-3-fluoropyridinyl-2-oxy-phenoxy]-propionic acid-(2-phenyl-2-oxy-ethyl) ester.

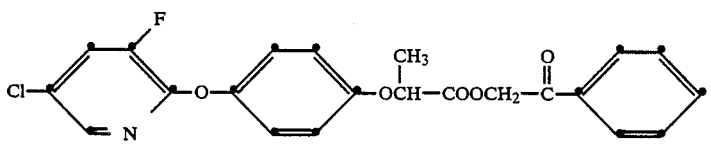

A mixture of 10.68 g (0.032 mol) of sodium-2-[4-(5-chloro-3-fluoropyridin-2-yloxy)-phenoxy]-propionate and 6.1 g (0.032 mol) of phenacyl bromide (98%) in 30 ml of dimethylformamide is heated for 1 hour at 80° C. The reaction mixture is then poured into ice/water, and is extracted three times with ethyl acetate. The extracts are washed with brine, dried with magnesium sulfate, filtered, and concentrated by evaporation. The product obtained is purified in petroleum ether/ether (2:1) through a short silica gel column. After the solvent has been evaporated off, the yield is 12 g of product; $n_D^{35} = 1.5679$.

EXAMPLE 2

Production of (±)-2-[4-(5-chloro-3-fluoropyridin-2-yloxy)-phenoxy]-propionic acid-(2,2-dicyanovinyl) amide

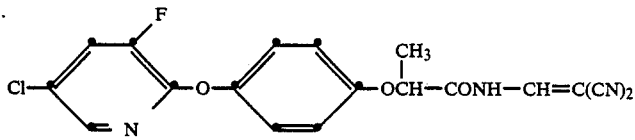

4.95 g (0.015 mol) of (±)-2-[4-(5-chloro-3-fluoropyridinyl-2-oxy)-phenoxy]-propionic acid chloride and 1.5 g (0.0155 mol) of 2,2-dicyanovinylamine are dissolved in 20 ml of acetonitrile in a sulfonating flask, and the solution is cooled to 5° C. with stirring. There are then added dropwise 2.2 ml (0.015 mol) of 1,8-diazabicyclo-[5.4.0]undec-7-ene (97%) dissolved in 5 ml of acetonitrile. The mixture is stirred at the same temperature for 1 hour, and the temperature is subsequently allowed to rise to 20° C. After 16 hours, the reaction mixture is poured onto ice, and 1 ml (0.015 mol) of methanesulfonic acid is added. The mixture is afterwards extracted twice with ethyl acetate; the extracts are then washed with brine, dried with magnesium sulfate, filtered, and concentrated by evaporation. The crude product is purified in ethyl acetate/hexane (1:1) through a short silica gel column to thus obtain, after removal of the solvent by evaporation, 5.0 g (86%) of the title product; m.p. 129°–131° C.

EXAMPLE 3

Production of (±)-2-[4-(5-chloro-3-fluoropyridinyl-2-oxy)-phenoxy]-propionic acid methoxyamide

1.7 g (0.02 mol) of O-methyl-hydroxylamine hydrochloride, 5.6 ml (0.04 mol) of triethylamine and 30 ml of toluene are cooled with stirring in a sulfonating flask to 5° C., and there are then added dropwise 4.95 g (0.015 mol) of (±)-2-[4-(5-chloro-3-fluoropyridinyl-2-oxy)-phenoxy]-propionic acid chloride in 15 ml of toluene. The reaction mixture is subsequently stirred for a further 3 hours at room temperature; it is afterwards poured into ice/water, and extracted three times with ethyl acetate. The extracts are washed with brine, dried with magnesium sulfate, filtered, and concentrated by evaporation. The yield is thus 3.9 g of an oil which crystallises on being stirred up in ether; m.p. 103°–105° C.

EXAMPLE 4

Production of 2-[4-(3-fluoro-5-trifluoromethylpyridyl-2-oxy)-phenoxy]-propionic acid-[2-(0,0-dimethylphosphonyl)-ethyl] ester

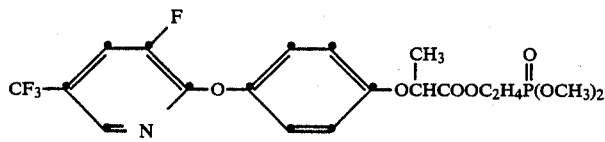

7.7 g (0.05 mol) of 2-hydroxyethyl-0,0-dimethylphosphonate are placed together with 6.9 ml (0.05 mol) of triethylamine and a spatula-tip of 4-piperadinopyridine into 130 ml of ethyl acetate. There are then added dropwise at room temperature, with stirring, 17.9 g (0.05 mol) of 2-[4-(3-fluoro-5-trifluoromethylpyridyl-2-oxy)-phenoxy]-propionic acid chloride in 20 ml of ethyl acetate. The reaction mixture is stirred for 1 hour at 30°14 35° C. and for 1 hour under refluxing conditions; the mixture is subsequently allowed to cool and is then filtered; the filtrate is afterwards treated with active charcoal, dried over sodium sulfate and concentrated by evaporation to thus obtain 22.1 g of a brown oil, which is finally chromatographed with $CH_2Cl_2/CH_3OH$ (95.5) through silica gel; yield 17.5 g of a light-yellow oil, $n_D^{30} = 1.4973$.

The following compounds are produced in a manner analogous to that of the above Examples.

TABLE 1

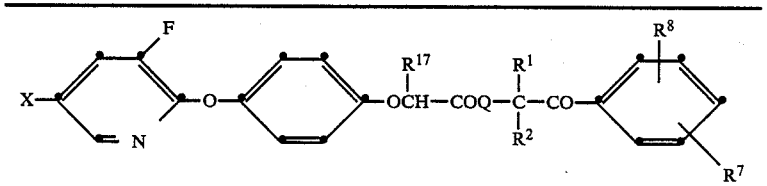

| No. | X | $R^{17}$ | Q | $R^1$ | $R^2$ | $R^8$ | $R^7$ | Physical properties |
|---|---|---|---|---|---|---|---|---|
| 1.01 | Cl | CH$_3$ | O | H | H | H | H | $n_D^{35}$ 1.5679 |
| 1.02 | Cl | H | O | H | H | H | H | |
| 1.03 | Cl | C$_2$H$_5$ | O | H | H | H | H | |
| 1.04 | CF$_3$ | C$_2$H$_5$ | O | H | H | H | H | |
| 1.05 | CF$_3$ | CH$_3$ | O | H | H | H | H | |
| 1.06 | CF$_3$ | H | O | H | H | H | H | |
| 1.07 | Cl | CH$_3$ | O | H | CH$_3$ | H | H | $n_D^{35}$ 1.5631 |
| 1.08 | Cl | CH$_3$ | O | H | H | 4-Cl | H | |
| 1.09 | Cl | CH$_3$ | O | H | H | 2-Cl | 6-Cl |
| 1.10 | Cl | CH$_3$ | O | H | H | 2-Cl | H |
| 1.11 | Cl | CH$_3$ | O | H | H | 2-OCH$_3$ | H |
| 1.12 | Cl | CH$_3$ | O | H | CH$_3$ | 2-Cl | H |
| 1.13 | Cl | CH$_3$ | O | H | CH$_3$ | 4-CH$_3$ | H |
| 1.14 | Cl | CH$_3$ | O | CH$_3$ | CH$_3$ | H | H |

TABLE 2

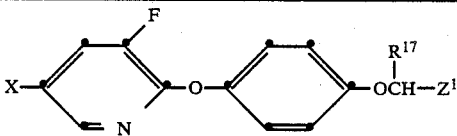

| No. | X | $R^{17}$ | $Z^1$ | Physical properties |
|---|---|---|---|---|
| 2.01 | Cl | H | CONH$_2$ | |
| 2.02 | Cl | CH$_3$ | CONH$_2$ | m.p. 162–164° C. |
| 2.03 | Cl | H | CONH—OCH$_3$ | |
| 2.04 | Cl | CH$_3$ | CONH—OCH$_3$ | m.p. 103–104° C. |
| 2.05 | Cl | CH$_3$ | CON(CH$_3$)OCH$_3$ | resinous oil |
| 2.06 | Cl | CH$_3$ | CONHOC$_2$H$_5$ | m.p. 78° C. |
| 2.07 | Cl | CH$_3$ | CONHCH$_3$ | m.p. 145–147° C. |
| 2.08 | Cl | CH$_3$ | CON(CH$_3$)CH$_3$ | |
| 2.09 | Cl | CH$_3$ | CONHOCH$_2$CH=CH$_2$ | m.p. 82–84° C. |
| 2.10 | Cl | CH$_3$ | CONH—CH=C(CN)$_2$ | m.p. 129–131° C. |
| 2.11 | Br | CH$_3$ | CONHOCH$_3$ | |
| 2.12 | Br | CH$_3$ | CONH—CH=C(CN)$_2$ | |
| 2.13 | CF$_3$ | CH$_3$ | CONHOCH$_3$ | m.p. 64° C. |
| 2.14 | CF$_3$ | CH$_3$ | CON(CH$_3$)OCH$_3$ | |
| 2.15 | CF$_3$ | CH$_3$ | CONH—CH=C(CN)$_2$ | |
| 2.16 | Cl | CH$_3$ | 1,2-oxazolidinyl-2-carbonyl | |
| 2.17 | CF$_3$ | CH$_3$ | 1,2-oxazolidinyl-2-carbonyl | |
| 2.18 | Cl | CH$_3$ | CSOCH$_3$ | |
| 2.19 | Cl | CH$_3$ | C(OCH$_2$SCH$_3$)=N—C$_6$H$_5$ | |
| 2.20 | Cl | CH$_3$ | 1,3-oxazolin-2-yl | |
| 2.21 | Cl | CH$_3$ | 4-methyl-1,3-oxazolin-2-yl | |
| 2.22 | CF$_3$ | CH$_3$ | CONH—OC$_2$H$_5$ | m.p. 89° C. |
| 2.23 | Cl | CH$_3$ | CONH—OCH$_2$CH=CHCl | m.p. 109–110° C. |
| 2.24 | Cl | CH$_3$ | CONHOCH$_2$—C(CH$_3$)=CH$_2$ | m.p. 85–86° C. |
| 2.25 | Cl | CH$_3$ | CONHC$_2$H$_5$ | m.p. 105–107° C. |

TABLE 3

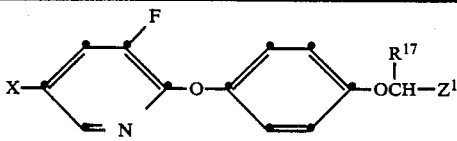

| No. | X | R$^{17}$ | Z$^1$ | Physical properties |
|---|---|---|---|---|
| 3.01 | Cl | CH$_3$ | —COOCH$_2$P(O)(OC$_2$H$_5$)$_2$ | |
| 3.02 | Cl | CH$_3$ | —COOCH$_2$P(O)(OCH$_3$)$_2$ | n$_D^{30}$ 1.5317 |
| 3.03 | Cl | CH$_3$ | —COOCH$_2$CH$_2$P(O)(OC$_2$H$_5$)$_2$ | |
| 3.04 | Cl | CH$_3$ | —COOCH$_2$CH$_2$P(O)(OCH$_3$)$_2$ | |
| 3.05 | Cl | CH$_3$ | —COOCH$_2$CH$_2$CH$_2$P(O)(OC$_2$H$_5$)$_2$ | |
| 3.06 | Cl | CH$_3$ | —COOCH$_2$—CH(CH$_3$)P(O)(OC$_5$H$_2$)$_2$ | |
| 3.07 | Cl | CH$_3$ | —COOCH$_2$P(O)(OCH$_3$)$_2$ | |
| 3.08 | Cl | H | —COOCH$_2$P(O)(OCH$_3$)$_2$ | |
| 3.09 | Cl | CH$_3$ | —COOCH(CH$_3$)P(O)(OCH$_3$)$_2$ | |
| 3.10 | Cl | CH$_3$ | —COOC(CH$_3$)$_2$P(O)(OCH$_3$)$_2$ | |
| 3.11 | Cl | CH$_3$ | —COOCH$_2$P(O)(OCH$_3$)CH$_3$ | |
| 3.12 | CF$_3$ | CH$_3$ | —COOCH$_2$P(O)(OC$_2$H$_5$)CH$_3$ | n$_D^{30}$ 1.4992 |
| 3.13 | Cl | CH$_3$ | —COOCH(CH$_3$)P(O)(OCH$_3$)CH$_3$ | |
| 3.14 | Cl | CH$_3$ | —COOCH(CH$_3$)P(O)(OC$_2$H$_5$)$_2$ | n$_n^{30}$ 1.5140 |
| 3.15 | CF$_3$ | CH$_3$ | —COOCH$_2$P(O)(OCH$_3$)$_2$ | |
| 3.16 | CF$_3$ | CH$_3$ | —COOCH$_2$CH$_2$P(O)(OCH$_3$)$_2$ | n$_D^{30}$ 1.4973 |

TABLE 4

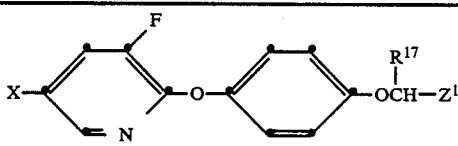

| No. | X | R$^{17}$ | Z$^1$ | Physical properties |
|---|---|---|---|---|
| 4.01 | Cl | CH$_3$ | 4,4-dimethyl-6-oxo-cyclohex-1-en-2-ol-1-ylcarbonyl | m.p. 83–85° C. |
| 4.02 | Cl | CH$_3$ | 5,5-dimethyl-3-oxo-cyclohex-1-en-1-yloxycarbonyl | oil |
| 4.03 | Cl | CH$_3$ | morpholinoethoxycarbonyl | n$_D^{30}$ 1.5378 |
| 4.04 | Cl | CH$_3$ | 2-oxo-tetrahydrofuryl-3-oxy-carbonyl | |
| 4.05 | Cl | CH$_3$ | isoxazolidin-2-yl-carbonyl | |
| 4.06 | CF$_3$ | CH$_3$ | isoxazolidin-2-yl-carbonyl | |
| 4.07 | Cl | CH$_3$ | 3-methyl-isoxazolidin-2-yl-carbonyl | |
| 4.08 | CF$_3$ | CH$_3$ | 3-methyl-isoxazolidin-2-yl-carbonyl | |
| 4.09 | Cl | CH$_3$ | 5-methyl-isoxazolidin-2-yl-carbonyl | |
| 4.10 | CF$_3$ | CH$_3$ | 5-methyl-isoxazolidin-2-yl-carbonyl | |

TABLE 5

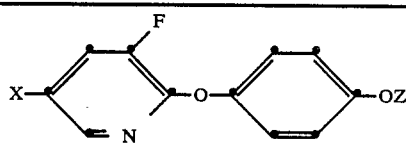

| No. | X | Z | Physical properties |
|---|---|---|---|
| 5.01 | Cl | CH$_2$COOCH$_3$ | m.p. 81–82° C. |
| 5.02 | CF$_3$ | CH$_2$COOCH$_3$ | |
| 5.03 | Br | CH$_2$COOCH$_3$ | |
| 5.04 | Cl | CH(C$_2$H$_5$)COOCH$_3$ | |
| 5.05 | CF$_3$ | CH(C$_2$H$_5$)COOCH$_3$ | |
| 5.06 | Cl | CH(CH$_2$OCH$_3$)COOCH$_3$ | |
| 5.07 | CF$_3$ | CH(CH$_2$OCH$_3$)COOCH$_3$ | |
| 5.08 | Cl | CH$_2$COOCH$_2$C≡CH | |
| 5.09 | CF$_3$ | CH$_2$COOCH$_2$C≡CH | |
| 5.10 | Cl | CH$_2$COOCH(CH$_3$)COOC$_2$H$_5$ | |
| 5.11 | CF$_3$ | CH$_2$COOCH(CH$_3$)COOC$_2$H$_5$ | |
| 5.12 | Cl | CH$_2$COSCH$_2$COOCH$_3$ | |
| 5.13 | CF$_3$ | CH$_2$COSCH$_2$COOCH$_3$ | |
| 5.14 | Cl | CH$_2$—C(CN)=CH$_2$ | |
| 5.15 | Cl | CH$_2$—C(COOCH$_3$)=CH$_2$ | |
| 5.16 | CF$_3$ | CH$_2$—C(COOCH$_3$)=CH$_2$ | |
| 5.17 | Cl | CH$_2$—C(COOC$_2$H$_5$)=CH$_2$ | m.p. 68° C. |
| 5.18 | Cl | CH(CH$_3$)COO(4-chlorobenzyl) | n$_D^{30}$ 1.5721 (racemate) |
| 5.19 | Cl | CH(CH$_3$)COO(4-chlorobenzyl) | m.p. 58–60° C. (2R) |
| 5.20 | Cl | CH(CH$_3$)COO(4-chlorobenzyl) | m.p. 63–64° C. (2 S) |
| 5.21 | CF$_3$ | CH(CH$_3$)COO(4-chlorobenzyl) | |
| 5.22 | Cl | CH(CH$_3$)COO(2-chlorobenzyl) | |

TABLE 6

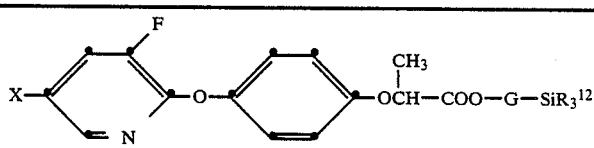

| No. | X | G | R$^{12}$ | Observations | Physical properties |
|---|---|---|---|---|---|
| 6.01 | Cl | —CH$_2$—CH$_2$— | CH$_3$ | 2R-enantiomer | n$_D^{35}$ 1.5181 [α]$_D^{20}$ = +37.0° (acetone) |
| 6.02 | Cl | —CH$_2$— | CH$_3$ | 2R-enantiomer | n$_D^{35}$ 1.5201 [α]$_D^{20}$ = +41.3° (acetone) |
| 6.03 | CF$_3$ | —CH$_2$— | CH$_3$ | racemate | m.p. 61–63° C. |

TABLE 6-continued

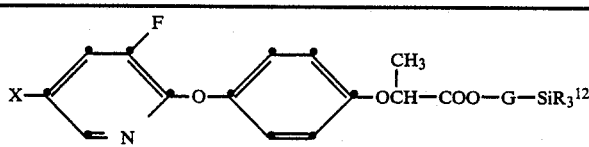

| No. | X | G | $R^{12}$ | Observations | Physical properties |
|---|---|---|---|---|---|
| 6.04 | $CF_3$ | $-CH_2-CH_2-$ | $CH_3$ | racemate | $n_D^{35}$ 1.4842 |
| 6.05 | Cl | $-CH_2-CH_2-$ | $CH_3$ | racemate | $n_D^{35}$ 1.5201 |
| 6.06 | Cl | $-CH_2-$ | $CH_3$ | racemate | $n_D^{35}$ 1.5155 |
| 6.07 | Cl | $-CH_2-$ | $C_2H_5$ | | |
| 6.08 | Cl | $-CH_2-CH_2-$ | $C_2H_5$ | | |
| 6.09 | Cl | $-CH(CH_3)-CH_2-$ | $CH_3$ | | |
| 6.10 | Cl | $-CH_2CH(CH_3)-$ | $CH_3$ | | |
| 6.11 | Cl | $-CH(CH_3)-$ | $CH_3$ | | |
| 6.12 | $CF_3$ | $-CH(CH_3)-$ | $CH_3$ | | |

TABLE 7

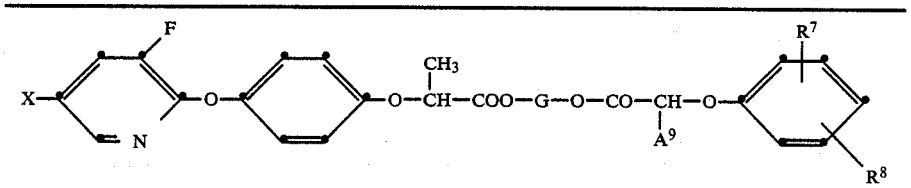

| No. | X | G | $A^9$ | $R^7$ | $R^8$ | Physical properties |
|---|---|---|---|---|---|---|
| 7.01 | Cl | $-CH_2-CH_2-$ | H | 4-Cl | H | $n_D^{35}$ 1.5547 |
| 7.02 | Cl | $-CH_2-CH_2-$ | H | 4-Cl | 2-Cl | |
| 7.03 | Cl | $-CH_2-CH_2-$ | $CH_3$ | 4-Cl | H | |
| 7.04 | Cl | $-(CH_2)_3-$ | H | 4-Cl | H | |
| 7.05 | Cl | $-CH_2-CH_2-$ | $CH_3$ | 4-Cl | 2-Cl | |
| 7.06 | Cl | $-CH_2-CH_2-$ | H | 4-Cl | 2-$CH_3$ | |
| 7.07 | $CF_3$ | $-CH_2-CH_2$ | H | 4-Cl | H | |
| 7.08 | $CF_3$ | $-CH_2CH_2-$ | H | 4-Cl | 2-Cl | |
| 7.09 | $CF_3$ | $-CH_2CH_2-$ | $CH_3$ | 4-Cl | H | |
| 7.10 | $CF_3$ | $-(CH_2)_3-$ | H | 4-Cl | H | |

TABLE 8

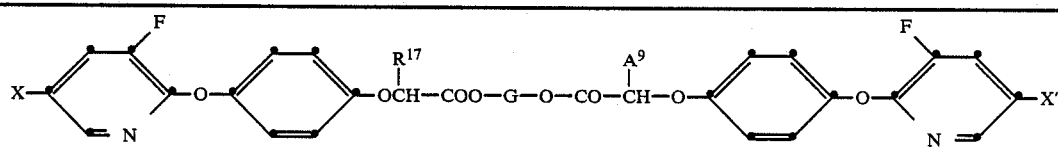

| No. | X | X' | $R^{17}$ | $A^9$ | G | Physical properties |
|---|---|---|---|---|---|---|
| 8.01 | Cl | Cl | $CH_3$ | $CH_3$ | $-CH_2-CH_2-$ | $n_D^{35}$ 1.5587 |
| 8.02 | Cl | Cl | $CH_3$ | H | $-CH_2-CH_2$ | |
| 8.03 | Cl | Cl | $CH_3$ | $CH_3$ | $-(CH_2)_3-$ | |
| 8.04 | Cl | Cl | $CH_3$ | $CH_3$ | $-CH(CH_3)CH_2-$ | |
| 8.05 | Cl | Cl | $CH_3$ | $CH_3$ | $-(CH_2)_4-$ | |
| 8.06 | Cl | Cl | $CH_3$ | $CH_3$ | $-CH(CH_3)-CH(CH_3)-$ | |
| 8.07 | $CF_3$ | $CF_3$ | $CH_3$ | $CH_3$ | $-CH_2-CH_2-$ | |
| 8.08 | $CF_3$ | $CF_3$ | $CH_3$ | H | $-CH_2-CH_2-$ | |
| 8.09 | $CF_3$ | $CF_3$ | $CH_3$ | $CH_3$ | $-(CH_2)_3-$ | |
| 8.10 | $CF_3$ | $CF_3$ | $CH_3$ | $CH_3$ | $-CH(CH_3)-CH_2-$ | |
| 8.11 | $CF_3$ | $CF_3$ | $CH_3$ | $CH_3$ | $-(CH_2)_4-$ | |
| 8.12 | $CF_3$ | Cl | $CH_3$ | $CH_3$ | $-CH_2CH_2-$ | |
| 8.13 | $CF_3$ | Cl | $CH_3$ | $CH_3$ | $-CH(CH_3)-CH_2-$ | |

EXAMPLE 5

Production of a formulation with liquid active ingredients of the formula I (%=percent by weight)

| Emulsion concentrates | (a) | (b) | (c) |
|---|---|---|---|
| 2-[4-(5-chloro-3-fluoropyridyl- | 20% | 40% | 50% |

| Emulsion concentrates | (a) | (b) | (c) |
|---|---|---|---|
| 2'-oxy)-phenoxy]-propionic acid methoxyamide | | | |
| calcium dodecylbenzenesulfonate | 5% | 8% | 5.8% |
| castor oil-polyethylene glycol ether (36 mols of ethylene oxide | 5% | — | — |
| tributylphenol-polyethylene glycol | — | 12% | 4.2% |

| Emulsion concentrates | (a) | (b) | (c) |
|---|---|---|---|
| (30 mols of ethylene oxide) cyclohexanone | — | 15% | 20% |
| xylene mixture | 70% | 25% | 20% |

Emulsions of any required concentration can be produced from concentrates of this type by dilution with water.

| Solutions | (a) | (b) | (c) | (d) |
|---|---|---|---|---|
| active ingredient according to Tables 1–8 | 80% | 10% | 5% | 95% |
| ethylene glycol-monomethyl ether | 20% | — | — | — |
| polyethylene glycol (M.W. 400) | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

The solutions are suitable for application in the form of very fine drops.

| Granulates | (a) | (b) |
|---|---|---|
| active ingredient according to Tables 1–8 | 5% | 10% |
| kaolin | 94% | — |
| highly dispersed silicic acid | 1% | — |
| attapulgite | — | 90% |

The active ingredient is dissolved in methylene chloride; the solution is subsequently sprayed onto the carrier, and the solvent is evaporated off in vacuo.

| Dusts | (a) | (b) |
|---|---|---|
| active ingredient from Tables 1–8 | 2% | 5% |
| highly dispersed silicic acid | 1% | 5% |
| talcum | 97% | — |
| kaolin | — | 90% |

Dusts ready for use are obtained by the intimate mixing together of the carriers with the active ingredient.

Formulation Examples for solid active ingredients of the formula I (%=percent by weight)

| Wettable powders | (a) | (b) |
|---|---|---|
| active ingredient from Tables 1–8 | 20% | 60% |
| sodium lignin sulfonate | 5% | 5% |
| sodium lauryl sulfate | 3% | — |
| sodium diisobutylnaphthalene sulfonate | — | 6% |
| octylphenolpolyethylene glycol ether (7–8 mols of ethylene oxide) | — | 2% |
| highly dispersed silicic acid | 5% | 27% |
| kaolin | 67% | — |

The active ingredient is well mixed with the additives and the mixture is thoroughly ground in a suitable mill. Wettable powders which can be diluted with water to give suspensions of the required concentration are obtained.

| Emulsion concentrate | |
|---|---|
| active ingredient from Tables 1–8 | 10% |
| octylphenol polyethylene glycol ether (4—5 mols of ethylene oxide) | 3% |
| calcium dodecylbenzenesulfonate | 3% |
| castor oil polyglycol ether (36 mols of ethylene oxide) | 4% |
| cyclohexanone | 30% |
| xylene mixture | 50% |

Emulsions of the concentration required can be obtained from this concentrate by dilution with water.

| Dusts | (a) | (b) |
|---|---|---|
| active ingredient from Tables 1–8 | 5% | 8% |
| talcum | 95% | — |
| kaolin | — | 92% |

Dusts ready for use are obtained by mixing the active ingredient with the carriers and grinding the mixture in a suitable mill.

| Extruder granulate | |
|---|---|
| active ingredient from Tables 1–8 | 10% |
| sodium lignin sulfonate | 2% |
| carboxymethylcellulose | 1% |
| kaolin | 87% |

The active ingredient is mixed and ground with the additives, and the mixture is moistened with water. This mixture is extruded and then dried in a stream of air.

| Coated granulate | |
|---|---|
| active ingredient from Tables 1–8 | 3% |
| polyethylene glycol (M.W. 200) | 3% |
| kaolin | 94% |

The finely ground active ingredient is evenly applied, in a mixer, to the kaolin moistened with polyethylene glycol. Dustfree coated granulates are obtained in this manner.

| Suspension concentrate | |
|---|---|
| active ingredient from Tables 1–8 | 40% |
| ethylene glycol | 10% |
| nonylphenolpolyethylene glycol ether (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. There is thus obtained a suspension concentrate from which can be produced, by dilution with water, suspensions of the concentration required.

EXAMPLE 6

Testing of the herbicidal action

Pre-emergence herbicidal action (inhibition of germination)

Immediately after sowing of the test plants in pots in a greenhouse, the surface of the soil is sprayed with an aqueous dispersion of the active ingredient, which has been prepared either from a 25% emulsion concentrate, or from a 25% wettable powder in the case of active ingredients which cannot be prepared as emulsion concentrates owing to inadequate solubility. Various concentrations are used, and the amount of active ingredient is calculated on the basis of kg per hectare. The pots are then kept in a greenhouse at 22°–25° C. with 50–70% relative humidity, and are regularly watered. The test results are evaluated after three weeks.

The tested compounds from Tables 1–8 exhibit a good to very good phytotoxic action against the monocotyledons used in the tests.

Post-emergence herbicidal action (contact herbicide)

A considerable number of weeds and cultivated plants, both monocotyledonous and dicotyledonous, are grown in pots in a greenhouse, and after emergence (in the 4- to 6-leaf stage) the plants are sprayed with an aqueous active-ingredient dispersion in varying dosages, expressed in kg of active ingredient per hectare, and the treated plants are kept at 24°–26° C. with 45–60% relative humidity. The test results are evaluated two weeks after the treatment.

In this case too, the tested compounds from Tables 1–8 have an excellent action against the monocotyledonous wild grasses used in the tests.

Reduction of growth of grasses

Seeds of the grasses Lolium perenne, Poa pratensis, Festuca ovina and Dactylis glomerata are sown in a soil/peat/sand mixture (6:3:1) in plastic trays and watered in the usual manner. The emerged grasses are cut back each week to a height of 4 cm, and are sprayed 40 days after sowing and 1 day after the last cutting with an aqueous spray liquor of in each case a compound of the formula I. The amount of active ingredient is equivalent to 0.05–2 kg of active ingredient per hectare. The growth of the grasses is compared, 10 and 21 days after application, with that of the untreated control specimens. The tested compounds from Tables 1–8 in an applied amount of 0.05 kg per hectare reduce the growth of the grasses by 18–32%.

What is claimed is:

1. A 3-fluoropyridyl-2-oxy-phenoxy derivative of the formula Ic

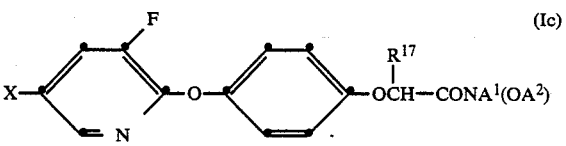

wherein X is chlorine, $A^2$ is methyl, ethyl, $C_3$–$C_4$-alkenyl or $C_3$–$C_4$-chloroalkenyl, $A^1$ is hydrogen or methyl and $R^{17}$ is methyl.

2. 4-(3-Fluoro-5-chloropyridyl-2-oxy)-phenoxyacetic acid methoxyamide according to claim 1.

3. α-[4-(5-Chloro-3-fluoropyridyl-2-oxy)-phenoxy]-propionic acid methoxyamide according to claim 1.

4. 2-[4-(5-Chloro-3-fluoropyridin-2-yloxy)-phenoxy]-propionic acid N-methoxy-N-methylamide according to claim 1.

5. A herbicidal or plant-growth regulating composition comprising, as active ingredient, a herbicidally or plant-growth regulating effective amount of a 3-fluoropyridyl-2-oxy-phenoxy derivative of the formula Ic according to claim 1, together with inert carrier material.

6. A method of selectively controlling gramineous weeds, which method comprises applying thereto or to the locus thereof a herbicidally effective amount of a 3-fluoro-pyridyl-2-oxy-phenoxy derivative of the formula Ic, according to claim 1.

7. A method of reducing the growth of plants, which method comprises applying thereto or to the locus thereof a herbicidally effective amount of a 3-fluoropyridyl-2-oxy-phenoxy derivative of the formula Ic, according to claim 1.

* * * * *